(12) United States Patent
Monroy et al.

(10) Patent No.: US 9,364,483 B2
(45) Date of Patent: Jun. 14, 2016

(54) PRE-MIX COMPOSITION FOR CATTLE

(71) Applicant: LABORATORIOS VIRBAC, Guadalajara, Jalisco (MX)

(72) Inventors: Jose Manuel Monroe Monroy, Jalisco (MX); Luis Gerardo Estrella Parraga, Jalisco (MX); Laurent Angeli, Vence (FR)

(73) Assignee: LABORATORIOS VIRBAC, Guadalajara (MX)

( * ) Notice: Subject to any disclaimer, the term of this patent is extended or adjusted under 35 U.S.C. 154(b) by 0 days.

(21) Appl. No.: 14/310,119

(22) Filed: Jun. 20, 2014

(65) Prior Publication Data

US 2015/0366875 A1 Dec. 24, 2015

(51) Int. Cl.
| | | |
|---|---|---|
| *A61K 9/14* | (2006.01) | |
| *A23K 1/18* | (2006.01) | |
| *A61K 31/55* | (2006.01) | |
| *A23K 1/16* | (2006.01) | |
| *A23K 1/14* | (2006.01) | |
| *A23K 1/175* | (2006.01) | |

(52) U.S. Cl.
CPC . *A61K 31/55* (2013.01); *A23K 1/14* (2013.01); *A23K 1/146* (2013.01); *A23K 1/1612* (2013.01); *A23K 1/1628* (2013.01); *A23K 1/1646* (2013.01); *A23K 1/175* (2013.01); *A23K 1/1813* (2013.01)

(58) Field of Classification Search
None
See application file for complete search history.

(56) References Cited

U.S. PATENT DOCUMENTS

| | | | |
|---|---|---|---|
| 5,624,710 A | 4/1997 | Grabitz | |
| 5,731,028 A | 3/1998 | Chevremont et al. | |
| 8,343,956 B2 * | 1/2013 | Krebs et al. | 514/214.02 |

FOREIGN PATENT DOCUMENTS

EP 0 197 188 10/1986

* cited by examiner

*Primary Examiner* — Robert T. Crow
*Assistant Examiner* — John P Nguyen
(74) *Attorney, Agent, or Firm* — Whitham, Curtis & Cook, P.C.

(57) ABSTRACT

The present invention concerns a premix composition for feeding cattle, comprising:
a) a premix carrier having an overall particle size comprised between 300 and 400 μm,
b) zilpaterol, and
c) a surface agent.

The present invention is also related to a method of increasing the rate of weight gain in cattle, comprising the administration to the cattle of feed additives consisting of a premix composition such as described, over a period of at least two weeks.

35 Claims, 4 Drawing Sheets

| Size (μm) | Volume In % |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |
| 0.105 | 0.00 |

| Size (μm) | Volume In % |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.00 |
| 0.417 | 0.00 |
| 0.479 | 0.00 |
| 0.550 | 0.00 |
| 0.631 | 0.00 |
| 0.724 | 0.00 |
| 0.832 | 0.00 |
| 0.955 | 0.00 |
| 1.096 | 0.00 |

| Size (μm) | Volume In % |
|---|---|
| 1.096 | 0.00 |
| 1.259 | 0.00 |
| 1.445 | 0.00 |
| 1.660 | 0.00 |
| 1.905 | 0.00 |
| 2.188 | 0.00 |
| 2.512 | 0.00 |
| 2.884 | 0.00 |
| 3.311 | 0.00 |
| 3.802 | 0.00 |
| 4.365 | 0.00 |
| 5.012 | 0.02 |
| 5.754 | 0.09 |
| 6.607 | 0.10 |
| 7.586 | 0.13 |
| 8.710 | 0.16 |
| 10.000 | 0.19 |
| 11.482 | 0.23 |

| Size (μm) | Volume In % |
|---|---|
| 11.482 | 0.23 |
| 13.183 | 0.29 |
| 15.136 | 0.36 |
| 17.378 | 0.45 |
| 19.953 | 0.56 |
| 22.909 | 0.70 |
| 26.303 | 0.85 |
| 30.200 | 1.02 |
| 34.674 | 1.20 |
| 39.811 | 1.39 |
| 45.709 | 1.58 |
| 52.481 | 1.76 |
| 60.256 | 1.94 |
| 69.183 | 2.12 |
| 79.433 | 2.29 |
| 91.201 | 2.47 |
| 104.714 | 2.67 |
| 120.226 | 2.90 |

| Size (μm) | Volume In % |
|---|---|
| 120.226 | 2.90 |
| 138.038 | 3.17 |
| 158.489 | 3.49 |
| 181.970 | 3.89 |
| 208.930 | 4.34 |
| 239.883 | 4.86 |
| 275.423 | 5.40 |
| 316.228 | 5.95 |
| 363.078 | 6.41 |
| 416.869 | 6.75 |
| 478.630 | 6.90 |
| 549.541 | 6.79 |
| 630.957 | 6.44 |
| 724.436 | 5.76 |
| 831.764 | 4.39 |
| 954.993 | 0.00 |
| 1093.478 | 0.00 |
| 1258.925 | 0.00 |

| Size (μm) | Volume In % |
|---|---|
| 1258.925 | 0.00 |
| 1445.440 | 0.00 |
| 1659.587 | 0.00 |
| 1905.461 | 0.00 |
| 2187.762 | 0.00 |
| 2511.886 | 0.00 |
| 2884.032 | 0.00 |
| 3311.311 | 0.00 |
| 3801.894 | 0.00 |
| 4365.158 | 0.00 |
| 5011.872 | 0.00 |
| 5754.399 | 0.00 |
| 6606.934 | 0.00 |
| 7585.776 | 0.00 |
| 8709.636 | 0.00 |
| 10000.00 | 0.00 |

*Figure 3A*

PRE-MIX COMPOSITION FOR CATTLE

FIELD OF THE INVENTION

The present invention relates to a premix for feeding animals, comprising a carrier, a beta agonist and a surfactant, said premix being formulated with smaller particles than usual, therefore presenting a better uniformity when mixed with food.

BACKGROUND

Premixes comprising active principles are currently used for orally delivering active compounds to animals, in particular to farm animals. These premixes are generally composed of a premix carrier of mineral or vegetal origin, a small quantity of active principles, and additives and excipients. They are easily incorporated to food, according to specific instructions of dosage, which allow the oral deliverance of the right dose of the active principle to the animals.

Drawbacks of this method are mainly the lack of homogeneity when the premix is incorporated into the animal food. Indeed, even if the blending is performed carefully, obtaining a homogeneous mix is challenging, due to the huge differences between the premix and the food ingredients, in terms of particles size, weight, hydrophilic and lipophilic features. Moreover, many active principles have electrostatic characteristics that make it difficult to homogenize the blend, since these compounds tend to accumulate in dead areas, on the walls of the blenders and of food containers.

These drawbacks are of particular relevance when the active components of the premix are beta agonists. Beta agonists are used to increase the rate of weight gain, to improve feed efficiency and increase carcass leanness during the last days on feed of breeding animals. Among them, the compound zilpaterol hydrochloride is widely used under the form of a premix, sold under its trade name ZILMAX® (animal feed containing zilpaterol hydrochloride). Zilpaterol is typically fed in the last three-six weeks of cattle's lives, with a brief period before death for withdrawal, which allows the drug to leave the animal's tissues. Process for its preparation is described in U.S. Pat. No. 5,731,028.

For these pharmaceutical ingredients, the recommended dose is about 5 to 20 grams per ton of animal food, and these extreme levels are very challenging in terms of homogeneity of the final mix. The lack of homogeneity in the animal food can induce a variation of consumptions of the active principles. If the proper dose is not administered in an uniform way in all animals, there will be a lack of uniformity in the benefits expected by the farmer.

Various strategies have been developed for obtaining more homogeneous premix and final mix.

U.S. Pat. No. 5,624,710 describes a premix wherein the granules supporting the active substances are coated with a water-soluble substance. It also describes the process for preparing said granular premix with particles having a diameter about the same size than the particles of animal feed, ranging between about 100 and 1,000 microns (μm).

The patent application EP 197 188 suggests the use of a non-ionic, physiologically compatible surfactant, to be sprayed during the blending of the premix, in order to limit the dust formation during the blending. These surfactants are for example monoesters of propylene glycol and of alimentary fatty acids. Moreover, this premix is characterized with a specific particle size of the support, between 300 and 800 microns, and a specific particle size of the active ingredient, between 50 to 200 microns.

The commercialized product ZILMAX® is produced by a process wherein the zilpaterol is dissolved in a fluid and sprayed onto the premix carrier (i.e. corn particles). The mixture is then dried and sieved. This long, expensive and environmental unfriendly process does not enable a suitable homogeneity of the mixture. Indeed, when this premix is blended with the animal feed, a variation coefficient staying above 10% in the final mix is observed, which is unacceptable.

On the contrary, in the present invention, zilpaterol is not dissolved in a fluid but is mixed in solid form with the premix carrier. The particle size of the premix carrier, and of the zilpaterol, are described hereunder. The present invention provides a very good homogeneity of the final mixture while being easier, faster and cheaper to put into practice.

BRIEF DESCRIPTION OF THE INVENTION

The present invention concerns a premix composition for administering zilpaterol to cattle, comprising:
a) a premix carrier having an overall particle size comprised between 300 and 400 μm,
b) zilpaterol, and
c) a surface agent.

The present invention is also related to a method of increasing the rate of weight gain in cattle, a method of increasing quality of meat in cattle, and a method of increasing carcass leanness in cattle, comprising the administration to the cattle of feed additives consisting of a premix composition according to the invention, over a period of at least two weeks.

BRIEF DESCRIPTION OF THE DRAWINGS

FIGS. 3A and 3B. Particle size distribution (size is expressed in μm) of the premix composition according to the invention. FIG. 3A—Table of the size distribution/FIG. 3B—Graph showing the size distribution.

FIG. 5B) C.V. of the mix "premix of the invention" and food.

DETAILED DESCRIPTION OF THE INVENTION

Figure 1:
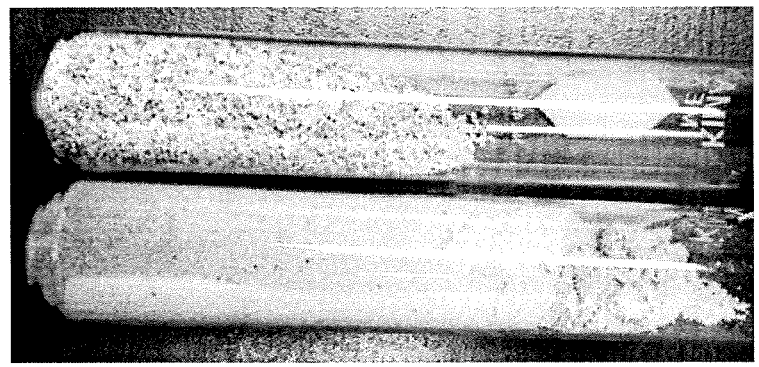
FIG. 1. Visual aspect of the ZILMAX® premix (upper tube) and the premix according to the invention (lower tube).

The present invention is related to a premix composition comprising:
a) a premix carrier having an overall particle size comprised between 300 and 400 μm,
b) zilpaterol, and
c) a surface agent.

In a specific aspect of the invention, the particles of the premix carrier are defined as follow:
 at least 90% of the particles have a size equal to or below 730 μm (D90);
 at least 50% of the particles have a size equal to or below 315 μm (D50);
 at least 10% of the particles have a size equal to or below 60 μm (D10).

The following terms are defined for a better understanding of the invention:

The term "premix carrier" designates edible, non-toxic compositions suitable for incorporation in livestock feed, that are the support for active principles. This support is chemically inert and is generally constituted of meals or flours, such as calcium carbonate, soybean mill run, rice mill hulls, wheat middlings, wheat bran, corn gluten, corn gluten meal, and other mill run byproducts.

The term "particle size" refers to the size of the particles in µm, as measured with an appropriate apparatus, such as a Beckman Coulter-SVM particle size analyzer or a Mastersizer 2000 particle size analyzer. Such apparatus use a technique of laser diffraction to measure the size of particles. It operates by measuring the intensity of light scattered, as a laser beam passes through a dispersed particles sample. This data is then analyzed to calculate the size of the particles that created the scattering pattern.

In the framework of the invention, "a particle size of x µm", can be interpreted as "a particle size of about x µm", wherein "about" means a value comprised within more or less 10%, or more or less 5% of the given value.

The term D10 refers to a value where at least 10% of the particles have a size less or equal to the given value. For instance a D10 value of 15 µm, means that at least 10% of the particles have a size equal to or below 15 µm.

The term D50 refers to a value where at least 50% of the particles have a size less or equal to the given value.

The term D90 refers to a value where at least 90% of the particles have a size less or equal to the given value.

The term "overall particle size" refers to the D50 value.

The phrase "the overall particle size is comprised between 300 and 400 µm" means that the D50 is from about 300 µm to about 400 µm, and in particular the specific embodiments wherein the premix carrier has a D50=300 µm or a D50=400 µm belong to the scope of the invention.

Naturally the given percentages of particles are not to be comprised strictly, but means "about at least 90%", "about at least 50%" and "about at least 10%". In particular a slight derivation, of less than 5%, of the number is tolerated. Therefore, for example, a premix composition comprising 89% of the particles having a size equal to or below 730 µm is comprised in the invention.

The terms "zilpaterol" "zilpaterol hydrochloride" and "zilpaterol HCL", used interchangeably, refer to a beta-adrenergic agonist, of CAS number 117827-79-9, and showing the chemical formula:

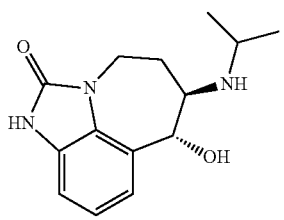 [SMILES: CC(C)N[C@@H]1CCn2c(=O)[nH]c3cccc(c32)[C@H]1O]

Zilpaterol is usually presented under crystallized form, a process of preparation is described in U.S. Pat. No. 5,731,028. Zilpaterol can be recrystallised to obtain the suitable granulometry. Such crystallisation is performed using usual solvents such as:
  polar aprotic solvent such as ethyl acetate, dichloromethane, acetone, or
  polar protic solvent, such as methanol, ethanol, isopropanol . . . .

The term "surface agent" or "surfactant", used interchangeably, refers to compounds that lower the surface tension (or interfacial tension) between two liquids or between a liquid and a solid. Non-ionic surfactants that do not ionize in water are preferred. Various types can be distinguished according to their chemical nature: ester bond (R—CO—O—R'), ether bond (R—O—R') or amide bond.

In a specific aspect of the invention, the premix composition comprises zilpaterol, wherein the particles of zilpaterol present the following size features:
  at least 90% of the particles have a size equal to or below 177 µm;
  at least 50% of particles have a size equal to or below 101 µm;
  at least 10% of particles have a size equal to or below 15 µm.

Said specific crystallized anhydrous zilpaterol is obtained from crystallisation using usual solvents such as described above. Zilpaterol can also be micronized with a suitable apparatus to obtain the desired size distribution.

In a particular aspect of the invention, the particles of zilpaterol can be much smaller, and in particular can be defined as follow:
  at least 90% of the particles have a size equal to or below 15 µm;
  at least 50% of particles have a size equal to or below 5 µm;
  at least 10% of particles have a size equal to or below 2 µm.

Zilpaterol

Zilpaterol is present in the premix composition under a crystallized form. According to a specific embodiment of the invention, zilpaterol is present in the premix composition at a concentration ranging from about 4% to about 5% in weight, related to the total weight of the composition.

Premix Carrier

As presented above, the premix carrier is the inert support for the active principle zilpaterol.

In a specific embodiment of the invention, the premix carrier is of mineral or vegetal origin. Preferably, the premix carrier is obtained from corn, and most preferably from corn cobs. Indeed, a corn cob has the ability to absorb up to seven times its own weight, which confers him excellent properties as a carrier. Furthermore, it is safe for animals, ecologically friendly and biodegradable.

According to a specific embodiment of the invention, the premix carrier is present in the premix composition at a concentration ranging from about 80% to about 85% in weight, related to the total weight of the premix composition.

Surface Agents

It has been shown in EP 197 188 that addition of physiologically compatible, non-ionic surface agents to premix composition allows a better homogenization of the blend. Typically, the surface agent is sprayed during the process of blending the premix carrier and zilpaterol.

In particular, a process for preparing the premix composition comprises at least the following steps:
  blending the premix carrier and zilpaterol for 5 to 20 minutes;
  spraying over the mixture the surface agent.

According to a first aspect of the invention, the surface agent is an ionic surface agent; the man skilled in the art knows various ionic surface agents that can be spayed over the premix composition, in particular:
  Among the anionic surfactants such as sulfate, sulfonate, phosphate esters, and carboxylates, the man skilled in the art will choose for instance ammonium lauryl sulfate, sodium lauryl sulfate, sodium dodecyl sulfate (SDS), alkyl-ether sulfates such as sodium laureth sulfate, sodium myreth sulfate, docusates such as dioctyl sodium, sulfosuccinate, perfluorooctanesulfonate (PFOS), perfluorobutanesulfonate, linear alkylbenzene sulfonates (LABs), carboxylates such as sodium stearate, sodium lauroyl sarcosinate, perfluorononanoate, and perfluorooctanoate (PFOA or PFO).

Among the cationic surfactants such as primary, secondary, or tertiary amines, the man skilled in the art will choose for instance octenidine dihydrochloride, quaternary ammonium cation such as alkyltrimethylammonium salts, cetyl trimethylammonium bromide (CTAB) a.k.a. hexadecyl trimethyl ammonium bromide, cetyl trimethylammonium chloride (CTAC), cetylpyridinium chloride, benzalkonium chloride, benzethonium chloride, 5-bromo-5-nitro-1,3-dioxane, dimethyldioctadecylammonium chloride, cetrimonium bromide, and dioctadecyldimethylammonium bromide.

Among the zwitterionic surfactants the man skilled in the art will choose for instance (3[(3-Cholamidopropyl) dimethylammonio]-1-propanesulfonate) or lecithin.

According to a specific embodiment of the invention, the surface agent is non-ionic, and is chosen from the group consisting of: ricin oil; polyoxyethylene alkyl ethers, polyoxyethylene castor oil derivatives (usually named 'polyoxyl') which comprises agents such as Polyoxyl 5 castor oil, Polyoxyl 9 castor oil, Polyoxyl 15 castor oil, Polyoxyl 35 castor oil, Polyoxyl 40 castor oil, Polyoxyl 40 hydrogenated castor oil, Polyoxyl 60 castor oil, Polyoxyl 60 hydrogenated castor oil, monoesters of propylene glycol; monoesters of alimentary fatty acids; stearyl-2-lactyl acid; acetic, lactic, citric, tartaric, monoacetyl tartaric esters of mono- and -diglycerides of alimentary fatty acids; glycerol-polyethylene glycol ricinoleate; polyethylene glycol esters of soybean oil fatty acids; sorbitan esters such as sorbitanmonostearate; sorbitantristearate; sorbitanmonolaurate; sorbitanmonooleate, and sorbitanmonopalmitate; propylene glycol alginate, polyoxyethylene stearates, polyoxyethyleneglycol esters, glycerol esters, glycerylmonooleate, polyoxyethylenesorbitan fatty esters, polysorbates, and combinations thereof.

In a preferred embodiment, the non-ionic surface agent is ricin oil. In another preferred embodiment, the non-ionic surface agent is polyoxyl.

In another preferred embodiment, the surface agent is present in the premix composition at a concentration ranging from about 2% to about 20% in weight, preferably from 5% to 15%, and more preferably from 8 to 10%, related to the total weight of the composition.

In a specific embodiment, the density of the premix composition is comprised between 200 g/l to 400 g/l.

In a preferred embodiment of the invention, the premix composition comprises at least the following relative amounts of components:
from 80% to 85% of premix carrier;
from 4% to 5% of zilpaterol; and
from 2% to 20% of surface agent.

In a specific embodiment, the premix composition may also include optional ingredients such as tackifiers, antioxidants, vitamins, preservatives, colorings, flavorings, minerals, other dietary supplements, and the like.

In a preferred embodiment, the premix composition comprises:
a) from 80% to 85% of corn cobs;
b) from 4% to 5% of zilpaterol; and
c) from 2% to 20% of Polyoxyl, and the particles of the premix composition are defined as follow:
at least 90% of the particles have a size equal to or below 730 µm;
at least 50% of the particles have a size equal to or below 315 µm;
at least 10% of the particles have a size equal to or below 60 µm.

In a preferred embodiment, the premix composition comprises:
a) from 80% to 85% of corn cobs;
b) from 4% to 5% of zilpaterol; and
c) from 2% to 20% of Polyoxyl,
and the particles the particles of zilpaterol present the following size features:
at least 90% of the particles have a size equal to or below 15 µm;
at least 50% of particles have a size equal to or below 5 µm;
at least 10% of particles have a size equal to or below 2 µm.

Uses of the Premix Composition

The premix composition of the invention is intended to be mixed with food for cattle, in order to administer the right daily dose of zilpaterol to said cattle. The recommended final concentration of zilpaterol in the finished food is about 6 ppm.

Food for cattle is mainly composed of high grains and roughage. Presence of roughage is important in particular in the introductory period, then grains can be increased slowly so that the gastro-intestinal tract has an opportunity to adapt to the increased starch content of the diet. Examples of high grains include, in a non-limitative manner, cottonseed meal, soybean meal, sunflower meal barley corn, oats, sorghum, and wheat.

The usual process for blending the premix composition and the food comprises generally two successive steps:
a first dilution comprising the addition of 125 g of premix to 99,875 kg of grounded grain or a mineral powder, and
a second dilution of 100 kg of the "first step mix" with 900 kg of food.

Examples 2 and 3 below present a process for blending the premix composition and the food in two successive steps.

Advantageously, the premix composition of the invention is mixed homogeneously with the food, and animals get the right dose of zilpaterol, when instructions of mixing are carefully followed. Typically, the amount of zilpaterol consumed daily will range from 60 to 90 mg by head.

The present invention is related to a method of increasing the rate of weight gain in cattle, comprising the administration to the cattle of feed additives consisting of any premix composition as described above, over a period of at least two weeks.

The present invention is also related to a method of increasing quality of meat in cattle, comprising the administration to the cattle of feed additives consisting of any premix composition as described above, over a period of at least two weeks.

The present invention is also related to a method of increasing carcass leanness in cattle, comprising the administration to the cattle of feed additives consisting of any premix composition as described above, over a period of at least two weeks.

In a specific embodiment, the administration of the premix composition is interrupted at least three days before death, allowing the drug to leave the animal's tissues before slaughter.

EXAMPLES

Example 1

Preparation of the Premix Composition

In an horizontal mixer, 210 Kg of corn cobs were added along with 12.06 Kg of Zilpaterol HCl, and the mixing process was started, during 10 minutes, once a proper visual uniformity was reached. 25 Kg of Polyoxyl 35 were added by spraying over the premix, while the mixer is running. Then the mixing process was stopped and the appearance of the premix was checked, once approved, the mixer was started again, and 3.8 Kg of corn cob was added to fit with the desired batch size.

Once verified the aspect of the premix, it was sampled and bottled in 5 Kg bags.

FIG. 1 shows the visual aspect of the premix composition such as obtained (lower tube), compared to the commercially available ZILMAX® (upper tube). The premix composition of the invention presents particles of small size, although the commercially available premix has bigger particles.

Figure 2:
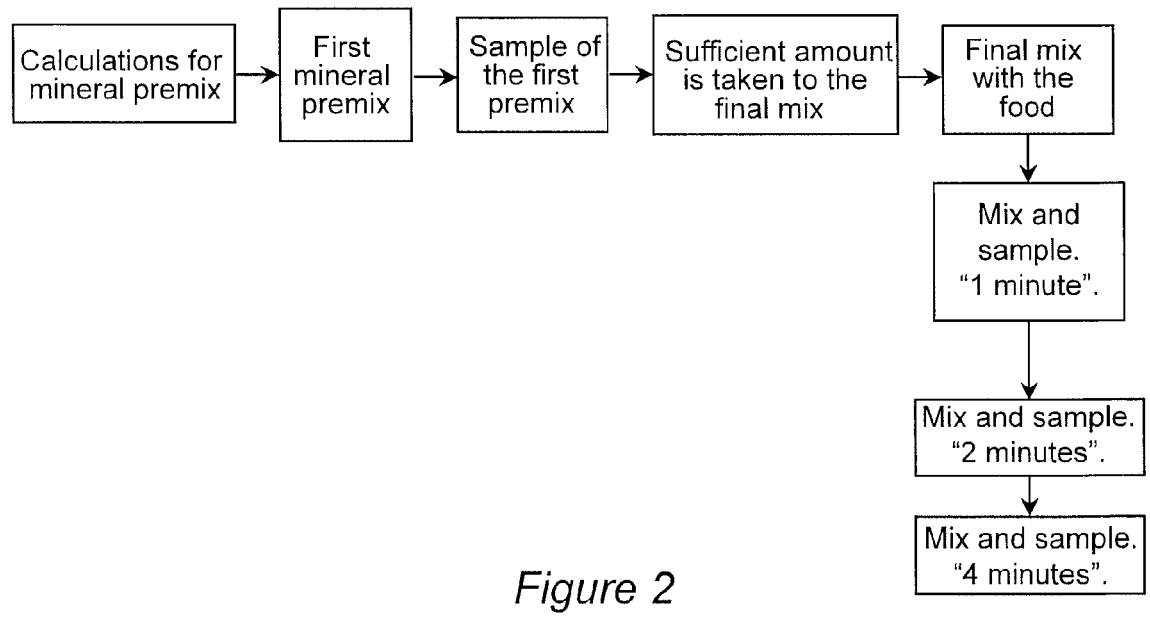
FIG. 2. Process for the preparation of the premix and samples.

FIG. 2 presents the process of preparation, as described above, and the sampling to test the coefficient of variation.

Figure 3B:
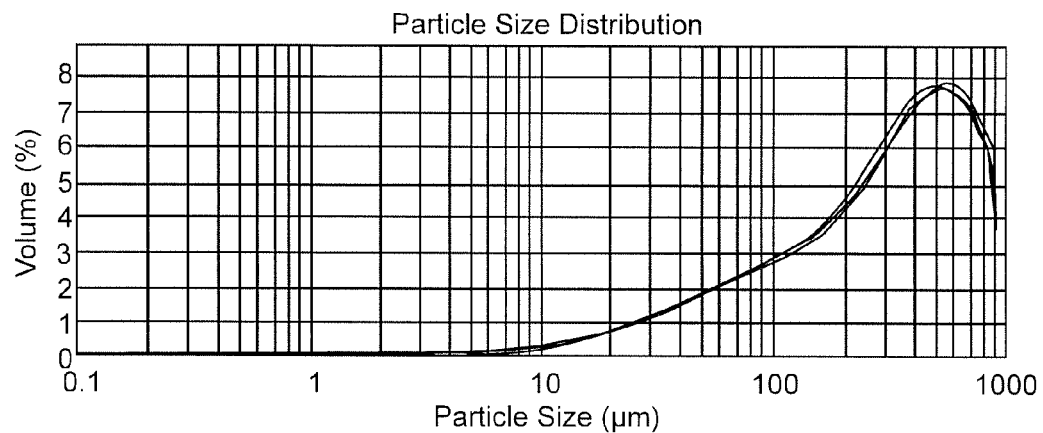

FIGS. 3A and 3B show the granulometry of the premix composition, i.e. the size distribution of the particles. As can be calculated from the table shown in FIG. 3A:

89.86% of particles have a size less or equal to 724,436 µm;
50.6% of particles have a size less or equal to 316,228 µm;
11.08% of particles have a size less or equal to 60,256 µm.

Example 2

First Step of Blending with a Mineral Powder

Using samples from the premix composition prepared as presented in example 1, a mixing test was made, comparing the formula of this invention with the formula of a commercial beta-agonist ZILMAX®, during the mixing process in an horizontal blender, mixing Zilpaterol HCl premixes with mineral salts.

84 g of the premix were mixed with 19.916 kg of a mineral mix, in a Lodige mixer with a working capacity of 30 kg.

4 samples in different points of the blender were taken at 1, 2 or 3 minutes.

Figure 4:
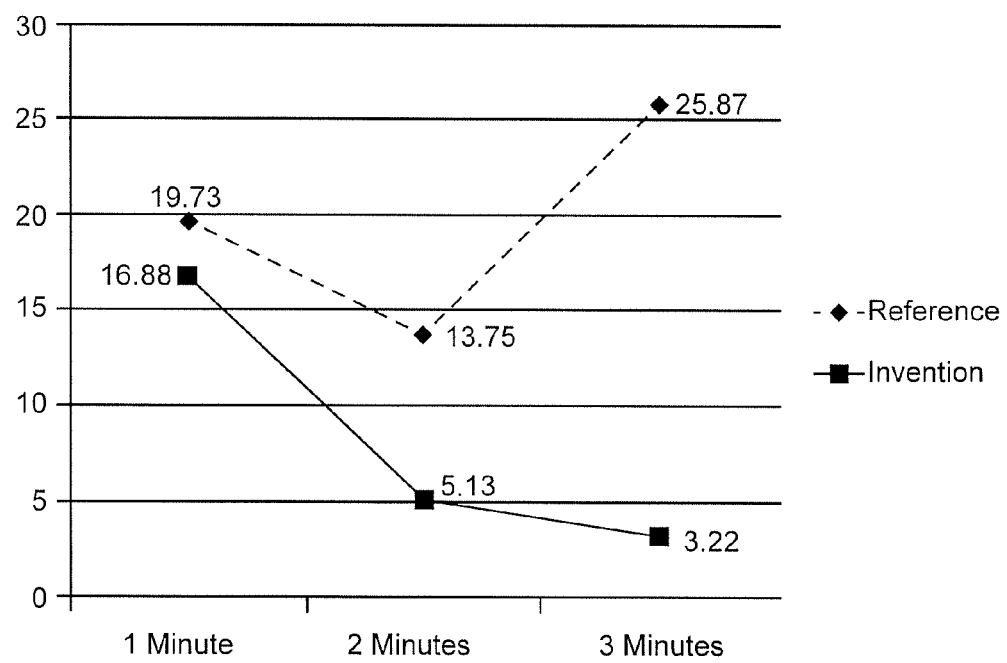
FIG. 4. Measure of variation coefficient at 1 minute, 2 minutes and 3 minutes for both ZILMAX® (Reference) and the premix composition according to the invention (Invention).

Surprisingly, the premix of example 1 gave quite better results than the referenced product, measured as Variation Coefficient, as expressed in the graphic shown in FIG. 4.

Variation coefficient is obtained by the following formula:

VC=Standard Deviation of samples concentration× 100/average of samples concentration "Samples concentration" designates the concentration of Zilpaterol HCl, obtained when performing a UPLC analysis with a validated analytical method.

It can be observed that the mixing profile of the premix composition is better than the one of ZILMAX®, reaching outstanding Variation Coefficients, 10% being considered as a good mixing and 5% as excellent. The Variation Coefficient reached at 3 minutes is remarkably good for the premix of the invention.

Example 3

Second Step of Blending with Food 20 kg of the mineral powder loaded with premix compositions were mixed with 280 kg of food.

Figure 5A:
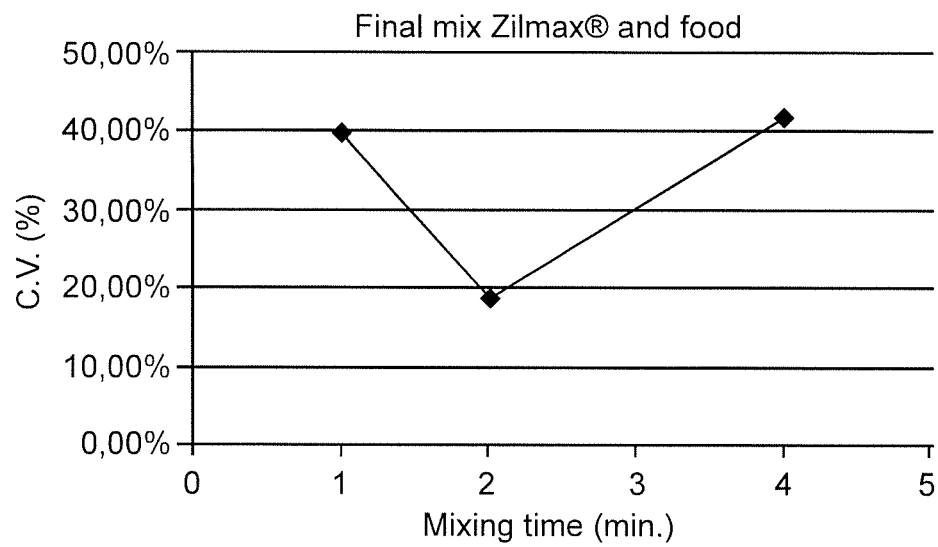
FIGS. 5A and 5B. Coefficient of variation (C.V.) in function of the mixing time of the final mix (food+premix)—FIG. 5A) C.V. of the mix ZILMAX® and food.
Figure 5B:
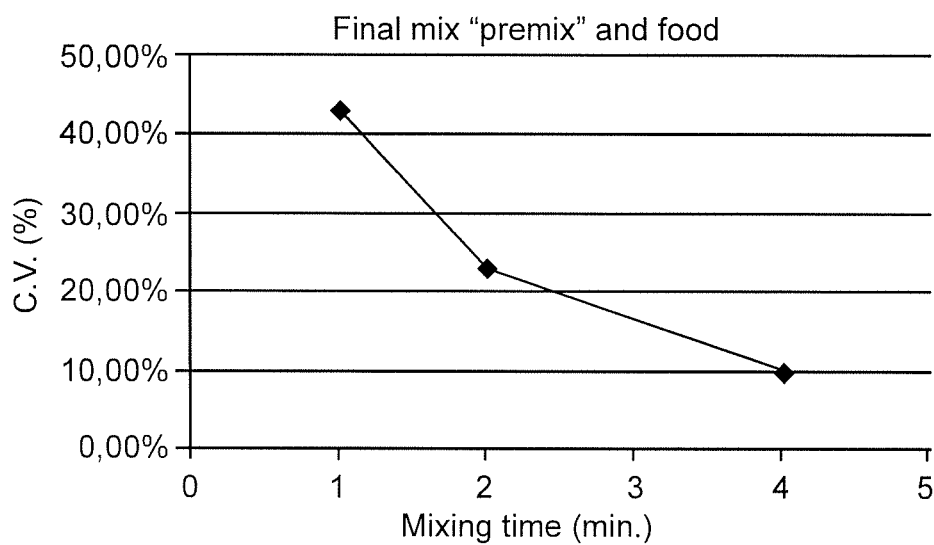

Three samples in different points of the blender were taken at 1, 2 or 4 minutes. The coefficient of variation was measured as shown above, and results are shown in FIGS. 5A and 5B; it appears that after one or two minutes of mixing, the final mixes have comparable qualities—40% then 20% of coefficient of variation. However, after four minutes of mixing, the final mix composed of food and premix of example 1 reaches a coefficient of variation of 10% only, although the final mix composed of food and ZILMAX® presents a coefficient of variation of 40%.

Example 4

Using product manufactured as explained in the Example 1, a stability study was carried out, under three conditions: 30° C. and 65% of relative humidity during a long term period of at least two years, 40° C. and 75% of relative humidity during 6 months, and 50° C. and 90% of relative humidity during a period of three months. Even under the most severe condition, the product remained stable, as per the graphic below:

REFERENCES

Patents

EP 0 197 188
U.S. Pat. No. 5,624,710
U.S. Pat. No. 5,731,028

The invention claimed is:

1. A premix composition comprising: a) a premix carrier comprising carrier particles, wherein at least 50% of the carrier particles have a size less or equal to about 400 µm, b) zilpaterol particles, and c) a surface agent.

2. The premix composition of claim 1 wherein the carrier particles of the premix carrier are defined as follow:
   at least 90% of the carrier particles have a size equal to or below about 730 µm;
   at least 50% of the carrier particles have a size equal to or below about 315 µm;
   at least 10% of the carrier particles have a size equal to or below about 60 µm.

3. A composition according to claim 1, wherein the zilpaterol particles present the following size features:
   at least 90% of the zilpaterol particles have a size equal to or below about 177 µm;
   at least 50% of the zilpaterol particles have a size equal to or below about 101 µm;
   at least 10% of the zilpaterol particles have a size equal to or below about 15 pm.

4. A composition according to claim 1, wherein the zilpaterol particles present the following size features:
   at least 90% of the zilpaterol particles have a size equal to or below about 15 µm;
   at least 50% of the zilpaterol particles have a size equal to or below about 5 µm;
   at least 10% of the zilpaterol particles have a size equal to or below about 2 µm.

5. A composition according to claim 1, wherein the zilpaterol particles are present in the said composition at a concentration ranging from about 4% to about 5% in weight, related to the total weight of the composition.

6. A composition according to claim 1, wherein the premix carrier is of mineral or vegetal origin.

7. A composition according to claim 6, wherein the premix carrier is obtained from corn cobs.

8. A composition according to claim 6, wherein the premix carrier is present in the said composition at a concentration ranging from about 80% to about 85% in weight, related to the total weight of the composition.

9. A composition according to claim 1, wherein the surface agent is chosen from ricin oil or polyoxyl.

10. A composition according to claim 9, wherein the surface agent is present in said composition at a concentration ranging from about 2% to about 20% in weight, related to the total weight of the composition.

11. A composition according to claim 1, wherein the density of said composition is comprised between 200 g/l to 400 g/l.

12. A composition according to claim 1, wherein the composition comprises the following relative amounts of components:
   a. from 80% to 85% of the premix carrier;
   b. from 4% to 5% of the zilpaterol particles;
   c. from 2% to 20% of the surface agent.

13. A composition according to claim 4, wherein the composition comprises the following relative amounts of components:
   a. from 80% to 85% of the premix carrier;
   b. from 4% to 5% of the zilpaterol particles;
   c. from 2% to 20% of the surface agent.

14. A method of increasing the rate of weight gain in cattle, comprising the administration to the cattle of feed additives consisting of a premix composition according to claim 1, over a period of at least two weeks.

15. A method of increasing quality of meat in cattle, comprising the administration to the cattle of feed additives consisting of a premix composition according to claim 1, over a period of at least two weeks.

16. A method of increasing carcass leanness in cattle, comprising the administration to the cattle of feed additives consisting of a premix composition according to claim 1, over a period of at least two weeks.

17. A method of increasing the rate of weight gain in cattle, comprising the administration to the cattle of feed additives consisting of a premix composition according to claim 4, over a period of at least two weeks.

18. A method of increasing quality of meat in cattle, comprising the administration to the cattle of feed additives consisting of a premix composition according to claim 4, over a period of at least two weeks.

19. A method of increasing carcass leanness in cattle, comprising the administration to the cattle of feed additives consisting of a premix composition according to claim 4, over a period of at least two weeks.

20. A method of increasing the rate of weight gain in cattle, comprising the administration to the cattle of feed additives consisting of a premix composition according to claim 13, over a period of at least two weeks.

21. A method of increasing quality of meat in cattle, comprising the administration to the cattle of feed additives consisting of a premix composition according to claim 13, over a period of at least two weeks.

22. A method of increasing carcass leanness in cattle, comprising the administration to the cattle of feed additives consisting of a premix composition according to claim 13, over a period of at least two weeks.

23. A composition according to claim 2, wherein the zilpaterol particles present the following size features:
   at least 90% of the zilpaterol particles have a size equal to or below about 15 μm;
   at least 50% of the zilpaterol particles have a size equal to or below about 5 μm;
   at least 10% of the zilpaterol particles have a size equal to or below about 2 μm.

24. A composition according to claim 2, wherein zilpaterol particles are present in the said composition at a concentration ranging from about 4% to about 5% in weight, related to the total weight of the composition.

25. A composition according to claim 2, wherein the premix carrier is of mineral or vegetal origin.

26. A composition according to claim 25, wherein the premix carrier is obtained from corn cobs.

27. A composition according to claim 25, wherein the premix carrier is present in the said composition at a concentration ranging from about 80% to about 85% in weight, related to the total weight of the composition.

28. A composition according to claim 2, wherein the surface agent is chosen from ricin oil or polyoxyl.

29. A composition according to claim 28, wherein the surface agent is present in said composition at a concentration ranging from about 2% to about 20% in weight, related to the total weight of the composition.

30. A composition according to claim 2, wherein the density of said composition is comprised between 200 g/l to 400 g/l.

31. A composition according to claim 2, wherein the composition comprises the following relative amounts of components:
   a. from 80% to 85% of the premix carrier;
   b. from 4% to 5% of the zilpaterol particles;
   c. from 2% to 20% of the surface agent.

32. A composition according to claim 23, wherein the composition comprises the following relative amounts of components:
   a. from 80% to 85% of the premix carrier;
   b. from 4% to 5% of the zilpaterol particles;
   c. from 2% to 20% of the surface agent.

33. A method of increasing the rate of weight gain in cattle, comprising the administration to the cattle of feed additives consisting of a premix composition according to claim 2, over a period of at least two weeks.

34. A method of increasing quality of meat in cattle, comprising the administration to the cattle of feed additives consisting of a premix composition according to claim 2, over a period of at least two weeks.

35. A method of increasing carcass leanness in cattle, comprising the administration to the cattle of feed additives consisting of a premix composition according to claim 2, over a period of at least two weeks.

* * * * *